(12) United States Patent
Hess et al.

(10) Patent No.: US 10,001,433 B2
(45) Date of Patent: Jun. 19, 2018

(54) METHOD FOR ROCKWELL HARDNESS TESTING OF TUBULARS POST WELLBORE INSTALLATION

(71) Applicant: Halliburton Energy Services, Inc., Houston, TX (US)

(72) Inventors: Joe E. Hess, Richmond, TX (US); Andy J. Cuthbert, Spring, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 326 days.

(21) Appl. No.: 14/930,133

(22) Filed: Nov. 2, 2015

(65) Prior Publication Data

US 2016/0178498 A1 Jun. 23, 2016

Related U.S. Application Data

(60) Provisional application No. 62/094,790, filed on Dec. 19, 2014.

(51) Int. Cl.
*G01N 3/44* (2006.01)
*E21B 47/024* (2006.01)
*E21B 47/00* (2012.01)

(52) U.S. Cl.
CPC .......... *G01N 3/44* (2013.01); *E21B 47/0006* (2013.01); *E21B 47/024* (2013.01)

(58) Field of Classification Search
CPC ............................. E21B 47/0006; G01N 3/44
See application file for complete search history.

(56) References Cited

U.S. PATENT DOCUMENTS

| 5,165,274 A * | 11/1992 | Thiercelin | E21B 49/006 73/152.59 |
| 7,669,668 B2 * | 3/2010 | Martinez | E21B 47/024 175/40 |
| 2012/0234600 A1* | 9/2012 | Lee | G01N 3/52 175/57 |
| 2013/0269931 A1* | 10/2013 | Badri | E21B 49/00 166/250.01 |

OTHER PUBLICATIONS

Corporate Consulting, Service & Instruments, Inc., "CCSi TechNotes: Basics of Rockwell Hardness Testing" Feb. 2006.*

* cited by examiner

*Primary Examiner* — Paul West

(57) ABSTRACT

Devices and methods are described for evaluating tubulars installed in a wellbore, which permit detection of wellbore construction errors. Errors in the hardness or grade of the material installed, e.g., in critical wellbores, could potentially affect the integrity of the wellbore and lead to catastrophic effects with respect to well control, pipe connection failure while running casing down-hole, or pipe body failure due to buckling or axial/triaxial failure during stimulation and production. Once tubulars are installed, the devices and methods permit testing the hardness of the steel or other material forming the tubulars. Determining the hardness of the tubulars may provide assurances or indications that remedial action may be appropriate to secure the wellbore. The devices and methods can be implemented to deliver a down-hole Rockwell hardness test in connection with logging while drilling technologies, with wireline tools, or in connection with other deployment mechanisms.

16 Claims, 4 Drawing Sheets

- 202 CONVEY TEST APPARATUS INTO THE WELLBORE TO POSITION THE PROBE ADJACENT A TARGET TUBULAR MEMBER
- 204 VERIFY A PERPENDICULAR ORIENTATION OF THE PROBE WITH RESPECT TO THE TARGET TUBULAR MEMBER
- 206 APPLY A MINOR LOAD TO THE TARGET TUBULAR MEMBER WITH AN INDENTING MEMBER OF THE PROBE
- 208 MEASURE A DEPTH, AREA OR OTHER CHARACTERISTIC OF A PERMANENT MINOR INDENTATION CREATED BY A MINOR LOAD
- 210 APPLY A MAJOR LOAD TO THE TARGET TUBULAR MEMBER WITH THE INDENTING MEMBER
- 212 MAINTAIN THE MAJOR LOAD FOR A PREDETERMINED DWELL TIME
- 214 RELIEVE THE MAJOR LOAD
- 216 MEASURE A DEPTH, AREA OR OTHER CHARACTERISTIC OF A PERMANENT MAJOR INDENTATION CREATED BY THE MAJOR LOAD
- 218 CALCULATE A HARDNESS VALUE FOR THE TARGET TUBULAR MEMBER FROM THE MEASUREMENTS OF THE MINOR AND MAJOR INDENTATIONS

METHOD FOR ROCKWELL HARDNESS TESTING OF TUBULARS POST WELLBORE INSTALLATION

CROSS-REFERENCE TO RELATED APPLICATIONS

This application claims priority to U.S. Provisional Application No. 62/094,790 filed Dec. 19, 2014, entitled "Method for Rockwell Hardness Testing of Tubulars Post Wellbore Installation" the disclosure of which is hereby incorporated by reference in its entirety.

BACKGROUND

1. Field of the Invention

The present disclosure relates generally to evaluating the integrity of structures installed in a wellbore, e.g., casing, liners and production tubing deployed in a hydrocarbon recovery wellbore. More particularly, embodiments of the disclosure relate to methods of hardness testing of metallic components subsequent to installing the metallic components in the wellbore.

2. Background

In the field of well construction in the oil at d gas industry, there has been occasion when one grade of the tubulars (casing, liner or completion tubing) has been mistaken for a different grade of tubular. This can occur through an error in material delivery from the vendor, poor casing design, lack of quality assurance/control (QA/QC) or a combination of all three. When wellbore conditions call for a particular grade of tubular, die result of installing a misidentified tubular can be that the weight or grade of steel being used is inadequate, or suspect at the very least. This may lead to a compromise in integrity of the tubular or premature failure during the lifecycle of the wellbore, particularly when the tubulars are installed in high-temperature-high-pressure (HTHP) wellbores and/or high hydrogen sulfide ($H_2S$) or carbon dioxide ($CO_2$) environments.

Often, tubulars are marked with color-coded bands, as set forth in API Spec 5CT, Section 11, marking, as an industry standard at one end that are intended to identify the grade of the tubulars and threaded connections or couplings. However, once the tubulars are installed in a wellbore, the color coded bands may not be visible, and the only recourse for determining the strength of the installed tubulars is to refer to the Mill Certificate. The Mill Certificate is a steel industry document that accompanies the shipments of tubulars when they depart the mill, and identify the tubulars by the manufacturing standards under which the tubulars were manufactured. Since the Mill Certificate may be separated from the tubulars before installation in the wellbore, or since the Mill Certificate may be inaccurate, reliance on the Mill Certificate is prone to error and is not a fail-safe method of establishing exactly what grade of tubulars are installed in the well. A need exists for devices and methods to test the hardness of the steel at any given point in the well while the pipe is in situ. The need exists, not necessarily for any specific well condition, rather in the event of a tubular failure, for assessing the failure mechanisms and for determining the appropriate hardness of down-hole steel structures. There may be both mechanical and geological reasons for assessing the hardness of down-hole steel structures, so a need exists for analysis tools for this type of analysis.

BRIEF DESCRIPTION OF THE DRAWINGS

The disclosure is described in detail hereinafter on the basis of embodiments represented in the accompanying figures, in which:

FIG. 2 is a partially cross-sectional schematic view of the down-hole hardness testing apparatus including an indenting member for engaging a structure to be tested in accordance with an example embodiment of the present disclosure;

FIGS. 3A and 3B are front views of tip members which may be installed on the indenting member of FIG. 2 for evaluating different types of structures in accordance with other example embodiments of the present disclosure;

FIG. 4 flow chart illustrating a process for evaluating down-hole structures including a plurality of indentation steps in accordance with example embodiments of the present disclosure; and FIGS. 5A, 5B and 5C are cross-sectional schematic views of an indenting member illustrating the sequence of indentation steps of FIG. 4.

DETAILED DESCRIPTION

Figure 1:
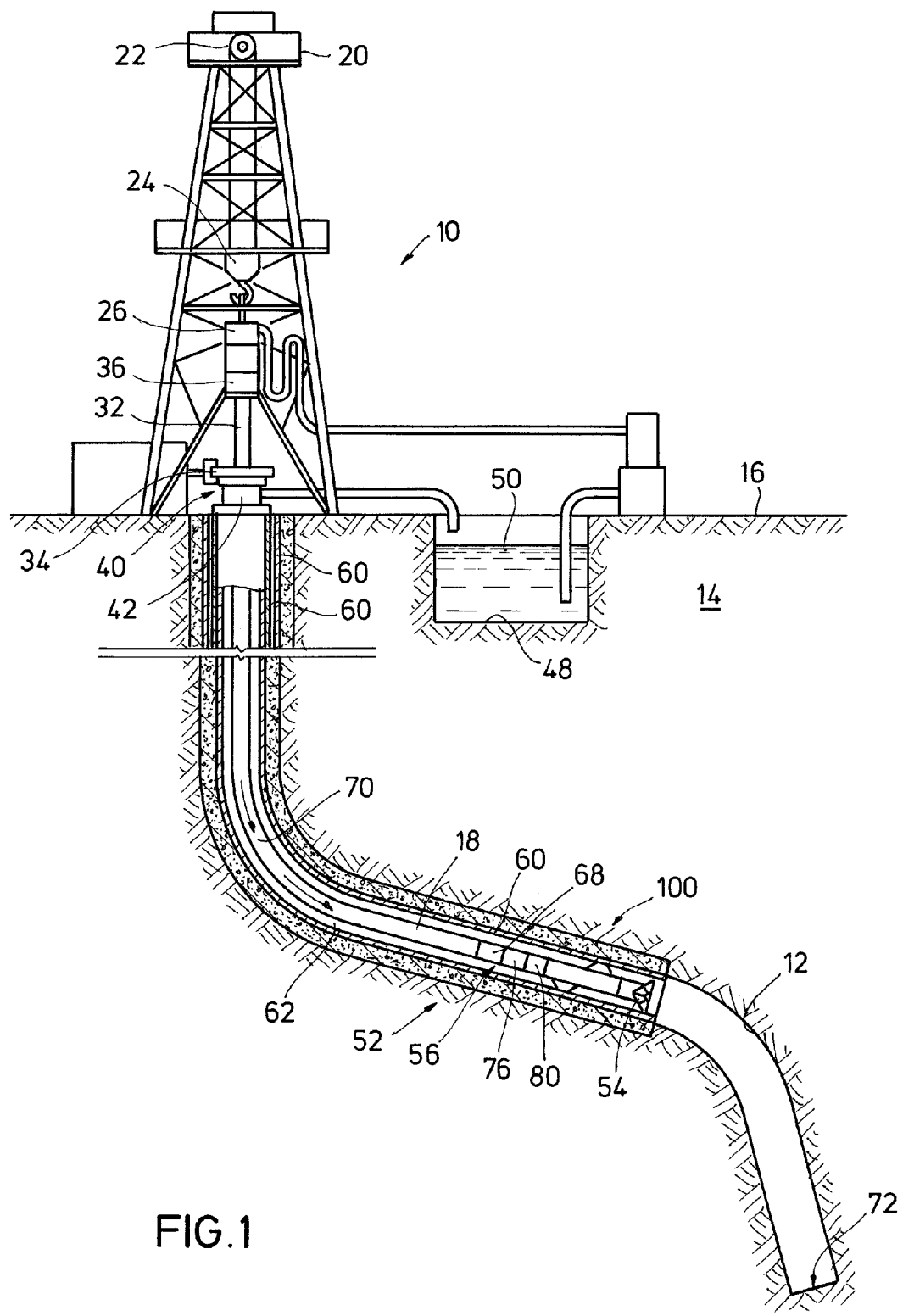
FIG. 1 is a partially cross-sectional side view of a drilling system including a down-hole hardness testing apparatus constructed in accordance with one or more exemplary embodiments of the disclosure.

In the following description, even though a Figure may depict an apparatus in a portion of a wellbore having a specific orientation, unless indicated otherwise, it should be understood by those skilled in the art that the apparatus according to the present disclosure may be equally well suited for use in wellbore portions having other orientations including vertical, slanted, horizontal, curved, etc. Likewise, unless otherwise noted, even though a Figure may depict an onshore or terrestrial operation, it should be understood by those skilled in the art that the apparatus according to the present disclosure is equally well suited for use in offshore operations. Further, unless otherwise noted, even though a Figure may depict a wellbore that is partially cased, it should be understood by those skilled in the art that the apparatus according to the present disclosure may be equally well suited for use in fully open-hole wellbores.

Hardness is a characteristic of a material, not a fundamental physical property. Hardness may be defined as the resistance to indentation, and may be determined by measuring a permanent depth of an indentation created in a target structure by the application of known loads. Generally, when using a fixed force (load) and a given indenter, the smaller the indentation, the harder the target material. An indentation hardness value may be obtained by measuring the depth or the area of the indentation. The Rockwell hardness test method, as defined in ASTM E-18, is often employed in the well construction industry for characterizing steel and other metals. The Rockwell method measures the permanent depth of indentation produced by a force/load on an indenter, and may be implemented down-hole by employing devices and methods described herein.

1. Description of Exemplary Embodiments

The present disclosure includes devices and methods for measuring and evaluating the hardness of downhole tubular members. Some of the devices and methods include a down-hole deployable probe with an indenting member thereon for applying minor and major loads to the target tubular member. A variance between depths of permanent indentations formed in the target tubular member by the applications of the minor and major loads may be measured to assess the hardness of the target tubular member.

FIG. 1 is an elevation view in partial cross-section of a wellbore drilling system 10 utilized to produce hydrocarbons from wellbore 12 extending through various earth strata in an oil and gas formation 14 located below the earth's surface 16. Wellbore 12 may be formed of a single bore or multiple bores (not shown), extending into the formation 14, and may be disposed in any orientation, such as the horizontal, vertical, deviated and may include portions thereof any combination of different orientations. Wellbore drilling system 10 includes a testing apparatus 100 disposed at a lower end of a conveyance 18. In the illustrated embodiment, the conveyance 18 comprises a drill string operable from the surface 16 to position the testing apparatus 100 within the wellbore 12. In other embodiments, other types of conveyances are contemplated including coiled tubing, production tubing, other types of pipe or tubing strings, wirelines, slicklines, and the like.

Drilling and production system 10 includes a drilling rig or derrick 20. Drilling rig 20 may include a hoisting apparatus 22, a travel block 24, and a swivel 26 for raising and lowering the drill string 18, another conveyance, and/or structure such as casing string. In FIG. 1, the conveyance 18 is a substantially tubular, axially extending drill string formed of a plurality of drill pipe joints coupled together end-to-end. Drilling rig 12 may include a kelly 32, a rotary table 34, and other equipment associated with rotation and/or translation of conveyance 18 within a wellbore 12. For some applications, drilling rig 18 may also include a top drive unit 36.

Drilling rig 20 may be located proximate to a wellhead 40 as shown in FIG. 1, or spaced apart from wellhead 40, such as in the case of an offshore arrangement (not shown) where the drilling rig 20 may be supported on an floating platform and coupled to a wellhead on the sea floor by a riser as appreciated by those skilled in the art. One or more pressure control devices 42, such as blowout preventers (BOPs) and other equipment associated with drilling or producing a wellbore may also be provided at wellhead 40 or elsewhere in the wellbore drilling system 10.

A working or service fluid source 48, such as a storage tank or vessel, may supply a working fluid 50 pumped to the upper end of the conveyance 18 or drill string and flow through conveyance 18. Working fluid source 48 may supply any fluid utilized in wellbore operations, including without limitation, drilling fluid, cementous slurry, acidizing fluid, liquid water, steam or some other type of fluid. Subsurface equipment 52 may be disposed within the wellbore 12, and may include equipment such as, for example, a drill bit 54 and bottom hole assembly (BHA) 56, and/or some other type of wellbore tool.

Wellbore drilling system 10 may generally be characterized as having a pipe system 58. For purposes of this disclosure, pipe system 58 may include casing, risers, tubing, drill strings, completion or production strings, subs, heads or any other pipes, tubes or equipment that attaches to the foregoing, such as conveyance 18. In this regard, pipe system 58 may also include one or more casing strings 60 that may be cemented in wellbore 12, such as the surface, intermediate and inner casings 60 shown in FIG. 1. An annulus 62 is formed between the walls of sets of adjacent tubular components, such as concentric casing strings 60 or the exterior of conveyance 18 and the inside wall of a casing string 60 or wellbore 12, as the case may be. The testing apparatus 100 is disposed adjacent a casing string 60 for assessing a hardness of the casing string 60. The conveyance 18 may be moved within to permit the drilling system 10 to perform other functions such drilling.

Where subsurface equipment 52 is used for drilling and conveyance 18 is a drill string, the lower end of the conveyance 18 may support the BHA 56, which may carry at a distal end the drill bit 54. During drilling operations, weight-on-bit (WOB) is applied as drill bit 54 is rotated, thereby enabling drill bit 54 to engage formation 14 and drill wellbore 12 along a predetermined path toward a target zone. In general, drill bit 54 may be rotated with conveyance 18 from rig 20 with top drive 36 or rotary table 34, and/or with a downhole mud motor 68 within BHA 56. The working fluid 50 pumped to the upper end of conveyance 18 flows through the longitudinal interior 70 of conveyance 18, through BHA 56, and exit from nozzles formed in drill bit 54. When the drill bit is positioned to rotate at a bottom end 72 of wellbore 12, working fluid 54 may mix with formation cuttings, formation fluids and other downhole fluids and debris to form a drilling fluid mixture that may then flow upwardly through the annulus 62 to return formation cuttings and other downhole debris to the surface 16.

Bottom hole assembly 56 and/or drill conveyance 18 may include various other tools such as mechanical subs and directional drilling subs. The BHA illustrated in FIG. 1 includes a power source 76, and measurement equipment 80, such as measurement while drilling (MWD) and/or logging while drilling (LWD) instruments, detectors, circuits, or other equipment operable to provide information about wellbore 12 and/or formation 14, such as logging or measurement data from wellbore 12. Measurement data and other information from tools 74 may be communicated using electrical signals, acoustic signals or other telemetry that can be converted to electrical signals at the rig 20 to, among other things, monitor the performance bottom hole assembly 56, and associated drill bit 54, as well as monitor the conditions of the environment to which the bottom hole assembly 56 is subjected. The measuring equipment 80 may also be communicatively coupled the testing apparatus 100, and may be operable for receiving, processing, and/or communicating hardness data provided by the testing apparatus 100 as described in greater detail below.

Although testing apparatus 100 is illustrated in a drilling system 10, one skilled in the art will recognize that aspects of the disclosure may be practiced in other downhole environments including production systems. For example, where the conveyance 18 is a wireline or slickline, e.g., the conveyance 18 may be employed to position the testing apparatus 100 adjacent a tubular member such as production tubing in a completion assembly to assess the hardness thereof.

Figure 2:
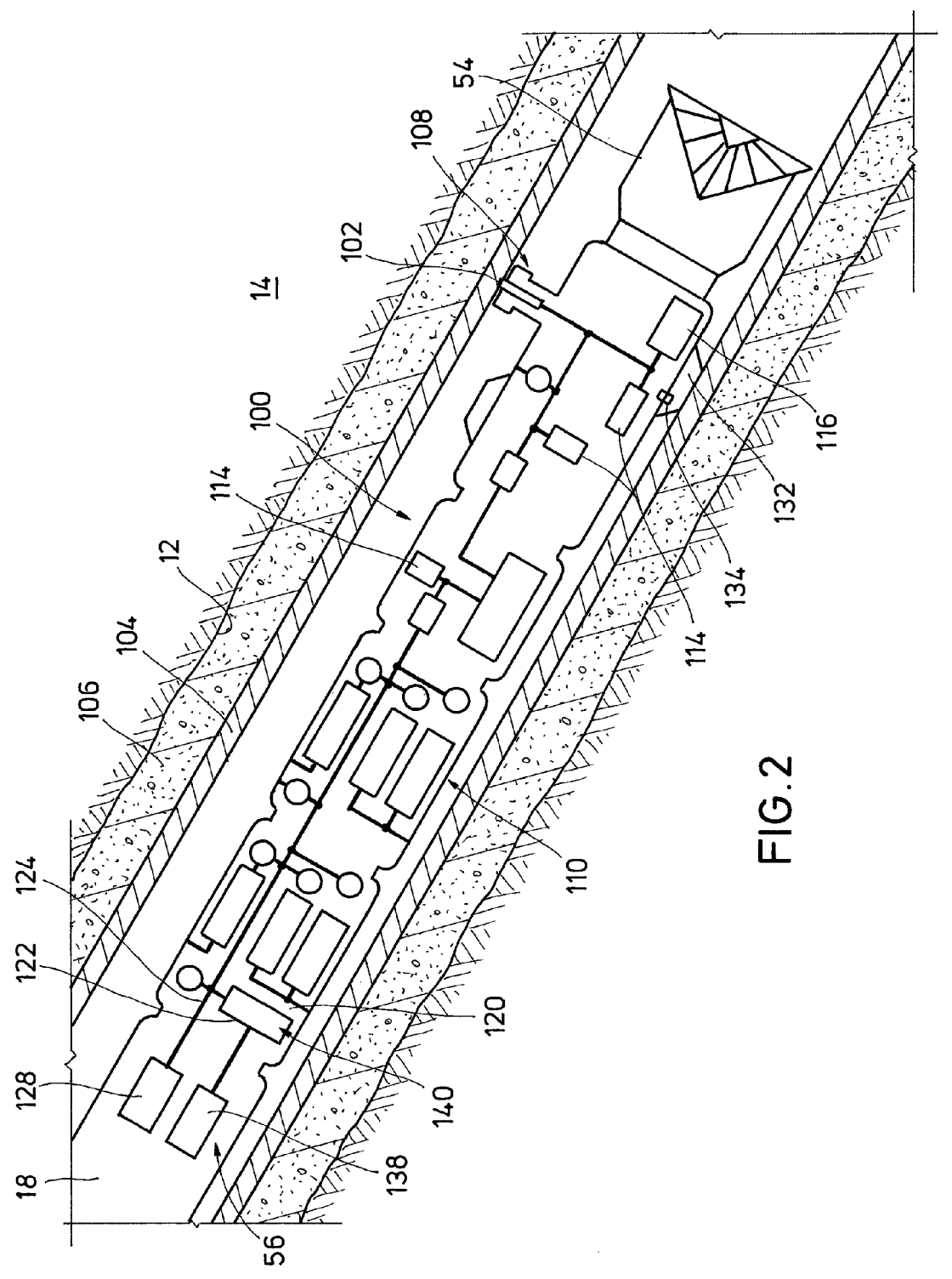

FIG. 2 is a partially cross-sectional schematic view of the down-hole hardness testing apparatus 100 including an indenting member 102 for engaging a target structure to be tested in accordance with an example embodiment of the present disclosure. The target structure is a tubular member 104 that extends within the wellbore 12 and is secured within the geologic formation 14 by a layer of cement 106. In some exemplary embodiments, the target tubular member 104 is a steel casing member that forms part of casing string 60 (FIG. 1). In some other embodiments (not shown), the target structures is production tubing, liner or other downhole structure recognized in the art. The testing apparatus 100 includes a probe 108 operably coupled to conveyance 18. As described above, conveyance 18 may include a drillstring, coiled tubing, electric line, wireline or other conveyance for deploying the probe 108 into the wellbore 12 and positioning the probe 108 adjacent the target tubular member 104. As illustrated, the probe 108 can he deployed on BHA 56 including a drill bit 54 powered by circulation of a drilling fluid as described above. In embodiments where the target structures to be tested are completion tubulars, which may be disposed in open hole environments, the probe 104 may be deployed on slimmer equipment, e.g., on a wireline, to permit maneuverability of the testing apparatus 100 and/or the probe 108.

As illustrated, the probe 108 may be disposed on a lateral side of the testing apparatus 100, and includes the indenting member 102 or other piston selectively extendable and retractable from the testing apparatus 100 and/or probe 108. In some exemplary embodiments, the indenting member 102 is controlled by a hydraulic system 110 disposed within the testing apparatus 100. As illustrated, the hydraulic system 110 includes a plurality of accumulators 114 that are controlled internally by a plurality of valves 116 such as solenoid valves. The valves 116 are operably coupled to a controller 120 that provides instructions to open and close the valves 116. In some embodiments, the controller 120 provides instructions to the valves 116 with electrical or other types of signals. In some embodiments, the controller 120 may include a computer having a processor 122 and a computer readable medium 124 operably coupled thereto. The computer readable medium 124 can include a nonvolatile or non-transitory memory with data and instructions that are accessible to the processor 122 and executable thereby. In one or more embodiments, the computer readable medium 124 is pre-programmed with instructions for opening and closing the valves 116 appropriately to impart major and minor loads to the target tubular member 104, as described in greater detail below, and to achieve other objectives. The controller 120 is also operable to receive feedback from hydraulic system 100 or other portions of the testing apparatus 100. For example, the controller 120 may receive signals representative of a distance traveled by the indenting member 102, readings from sensors (see inclination sensor 134 described below), or confirmation that certain steps have been completed.

Appropriately opening and closing the valves 116 results in extension and retraction of the indenting member 102, thereby forcing the indenting member 102 into the target tubular member 104 with predetermined minor and major forces as described in greater detail below. The accumulators 114 are attached to solenoids and are powered by a system pump (not shown), which may be disposed at the surface 16 (not shown). In some embodiments, the hydraulic system 110 of the testing apparatus 100 may be isolated from the flow of working fluid 50 (FIG. 1) with a flow diverter valve 128 during normal circulating operations. When hydraulic power is needed the diverter valve 128 is opened such that working fluid 50 flowing through the conveyance 18 may be provided to the hydrauliuc system 110.

In other embodiments, where the probe 108 is deployed on a wireline for example, the hydraulic system 110 may be replaced with an electromechanical system (not shown), which may include electric motors or other electromechanical actuators for moving the indenting member 102. When the probe 108 is deployed by slickline, a battery or other local power source may provide power to the actuator. When coiled tubing is used to deploy the probe 108, either s hydraulic system 110 or an electromechanical system (not shown) may be employed for deploying the probe 108 and operating the indenting member 102.

Additionally, the testing apparatus 100 may include at least one stabilizer 132 extending laterally therefrom in some embodiments. The stabilizer 132 maintains the indenting member 102 in a generally perpendicular inclination with respect to the target tubular member 104. In some embodiments, the stabilizer 132 is operable to maintain an inclination within 2 degrees of perpendicular to ensure precise loading of the target tubular member 104. In addition, testing apparatus 100 or stabilizer 132 may include one or more inclination sensors 134 operably coupled to the controller 120 to verify an appropriate inclination. The inclination sensor 134 may comprise accelerometers or other devices for evaluating the inclination of the testing apparatus as recognized in the art.

In some embodiments, the probe 108 of the testing apparatus 100 may be deployed down-hole as a component of, or coupled to measurement equipment 80 (FIG. 1), which may include a measure while drilling (MWD) or logging while drilling (LWD) system such as a modified GeoTap® IDS tool. The indenting member 102 could be operated, e.g., to perform a hardness test in a two-stage loading operation as described below, and the results of the hardness test could be communicated to the surface 16 with a communication unit 138 coupled to the controller 120. The communication unit 138 may an MWD telemetry system provided as part of the measurement equipment 80. In some embodiments, the communication unit 138 comprises a 2-way mud-pulse telemetry unit, operable to selectively deliver and receive information, and in some embodiments, the communication unit 138 comprises a wireless device such as a hydrophone or other types of transducers operable to selectively generate and receive acoustic signals. In some embodiments, the communication unit 138 can comprise other wired or wireless telemetry tools as will be appreciated by those skilled in the art. In other embodiments, the data obtained may be stored in a local memory 140 of the controller 120 until the testing apparatus 100 is removed from the wellbore 12.

As illustrated in FIGS. 3A and 3B, for example, a variety of indenting members 150, 152 are contemplated for use within the probe 108. A conical tip 154 (FIG. 3A) such as a conical diamond with a round tip may be employed for relatively harder target metals. In some embodiments, for relatively soft target metals, ball indenters (FIG. 3B) having a diameter "D" in the range from about 1/16 inch to about 1/2 inch may be employed. Generally, when selecting a Rockwell scale, a general guide is to select the scale that specifies the largest load and the smallest indenting member 102 (FIG. 2), 150, 152 possible without exceeding defined operation conditions and accounting for conditions that may influence the test result.

2. Example Methods of Operation

FIG. 4 is a flow chart illustrating a process 200 for evaluating down-hole target structures including a plurality of indentation steps in accordance with example embodiments of the present disclosure. As illustrated in FIG. 4 and FIGS. 5A-5C, and with continued reference to FIG. 2, the process 200 exemplary embodiments of methods of evaluating down-hole structures such as the target tubular member 104 are illustrated. Initially at step 202, an appropriate indenting member 102, 150, 152 may be selected, and the testing apparatus 100 may be deployed down-hole on any of the conveyances 18 described above. Next at step 204, a perpendicular inclination of the indenting member 102, 150, 152 with respect to the target tubular member 104 can be verified with the inclination sensor 134. In some embodiments, when an inclination of greater than 2 degrees from perpendicular is detected, the conveyance 18 or testing apparatus 100 may be manipulated to urge the testing apparatus 100 into the proper inclination before proceeding. In some embodiments, e.g., where an inclination of greater than 2 degrees (or outside another predetermined threshold) may not be readily corrected, the inclination sensor 134 can provide an inclination data associated with the readings, so that an appropriate correction factor may be determined or estimated, or so the reliability of the data obtained may be assessed. In some embodiments, where an inclination of greater than 2 degrees is detected, the testing apparatus 100 may be repositioned at another point in the wellbore 12 where a more appropriate inclination is achievable.

Once the desired inclination is verified, the controller 120 can command the hydraulic system 110 to urge the indenting member 102, 150, 152 to engage the target tubular member 104 and apply the minor load F0 (FIG. 5A) thereto (step 206). In some embodiments, the hydraulic system 110 is operable to deliver minor loads F0 in the range from about 3 $kg_f$ to about 10 $kg_f$ as specified in the "Regular" Rockwell scale, and in some embodiments minor loads F0 of up to about 200 $kg_f$ as specified in the macro scale (not part of ASTM E-18; see ASTM E-1) may be provided. The minor load F0 may be a preliminary test force, commonly referred to as preload. The minor load F0 causes the indenting member 102, 150, 152 to generate a minor indentation 302 (see FIG. 5A) in the target tubular member 104, that breaks through any surface finishes on the target tubular member 104 to reduce the effects of the surface finish. An appropriate minor load F0 may be pre-determined such that the minor load F0 is sufficient to break through the particular surface finish on the target tubular member 104 or other down-hole structure such that the particular indenting member 102, 150, 152 engages a core material of the target tubular member 104. The minor indentation 302 represents a zero datum or reference position from which subsequent positions are measured. At step 208, a depth, area or other characteristic of the minor indentation 302 may be measured, e.g., by evaluating a distance the indenting member 102, 150, 152 extended from the probe 108. Generally, it may be desirable to make measurements of indentations formed in flat perpendicular surfaces. However, since the target tubular member 104 is generally curved, the minor indentation 302 is formed in a concave surface. Because of the concavity, a predictably lower reading may be obtained than in a flat surface of the same material. Thus, a correction factor may be applied to the measurement of the depth, area or other measured characteristic of the minor cavity 302 (and other measurements described herein) by the controller 120 downhole, or by a processor (not shown) at the surface 16 in a post processing step.

After measuring the minor indentation 302, at step 210, an additional load, called the major load F1 is applied to the target tubular member 104 to reach the total required test load or combined load F0+F1 (see FIG. 5B). In some embodiments, a major load F1 may be provided such that the combined load F0+F1 (including the minor and major loads F0 and F1) may be in the range of about 15 $kg_f$ to about 150 $kg_f$, and in some embodiments the combined load F0+F1 may be in the range of about 500 $kg_f$ to about 3000 $kg_f$ (macro hardness). This combined load F0+F1 may be maintained for a predetermined amount of time (dwell time) at step 212 to allow for elastic recovery. The major load is then released at step 214 and a permanent or persisting major indentation 304 (see FIG. 5C) is defied in target tubular member 104. At step 216, the depth, area or other characteristic of the major indentation 304 may be measured against the position, depth, area or other characteristic of the minor indentation 302 derived from the minor load F0. In some embodiments, the variance "E" between the depth of the major indentation 304 and the minor indentation 302 may then be determined.

The variance "E" can be used to calculate a hardness value for the target tubular member 104 at step 218. For example, the variance "E" between minor indentation 302 and the major indentation 304 can be converted to a dimensionless hardness number, noted as HRA. Indentation hardness also correlates linearly with tensile strength (the penetration depth and hardness are inversely proportional), so verification or evaluation of the tensile strength of the target tubular member 104 may also be made by the preceding methodology.

In some embodiments of the procedure 200, one or more of the steps described above may be automatically executed in response to a sequence of instructions stored on the computer readable medium 124. For example, the controller 120 may execute the sequence of instructions to induce the application of the minor and major loads F0, F1 and the associated measurements described in steps 206 through 216 without any input from a user. In other embodiments, the user may transmit a distinct signal to the communication unit 138 to prompt the controller 120 to selectively apply each of the major and minor loads F0, F1 individually. In this manner, a user may select a desired force, indentation depth or other characteristic associated with the minor and major loads F0, F1, and may selectively or manually instruct the testing apparatus 100 to apply the minor and major loads F0, F1 at any time by manually sending instructions to the communication unit 138.

3. Aspects of the Disclosure

The aspects of the disclosure described in this section are provided to describe a selection of concepts in a simplified form that are described in greater detail above. This section is not intended to identify key features or essential features of the claimed subject matter, nor is it intended to be used as an aid in determining the scope of the claimed subject matter.

According to one aspect, the disclosure is directed to a method of evaluating down-hole structures. The method includes (a) conveying a testing apparatus having an indenting member into a wellbore to position the testing apparatus adjacent a target down-hole structure, (b) applying a major load to the down-hole structure with an indenting member of the testing apparatus to permanently form a major indentation in the target down-hole structure (c) measuring a characteristic of the major indentation, and (d) determining a hardness value for the target down-hole structure from the characteristic of the major indentation.

In some exemplary embodiments, the characteristic of the major indentation is a depth of the major indentation. In other embodiments, the characteristic of the major indentation is an area of the major indentation. In some embodiments, the method further includes applying, prior to applying the major load, a minor load to the indenting member to urge the indenting member to engage the target down-hole structure and to permanently form a minor indentation in the target down-hole structure. The method may include measuring a depth of the minor indentation, and determining a variance between the depth of the major indentation and the depth of the minor indentation to thereby determine the hardness value for the target down-hole structure. In some embodiments, the method further includes communicating at least one of the depth or other characteristic of the major indentation, the depth or other characteristic of the minor indentation, the variance between the depths or other characteristics of the major and minor indentations and the hardness value to a surface location from the testing apparatus in the wellbore. In some embodiments, the method further includes pre-determining the minor load such that the minor load is sufficient to break through a surface finish on the target down-hole structure such that the indenting member engages a core material of the target down-hole upon application of the preload.

In one or more embodiments, the method further includes maintaining the major load for a predetermined dwell time, wherein the dwell tune is predetermined to permit elastic recovery of the target down-hole test structure. The method may further include orienting the testing apparatus in the wellbore such that the indenting member engages the target down-hole structure in a generally perpendicular manner. In some embodiments, the testing apparatus is oriented to engage the target down-hole structure within 2 degrees of perpendicular. In some embodiments the indenting member engages a concave surface of the target down-hole structure, and wherein determining the hardness value for the target down-hole structure comprises applying a correction factor to accommodate for the concave surface.

According to another aspect, the disclosure is directed to a method of evaluating tubular members disposed in a wellbore. The method includes (a) conveying a testing apparatus into the wellbore to position the testing apparatus adjacent a target tubular member. (b) measuring a characteristic of the target tubular member with the testing apparatus, and (c) determining a hardness value for the target tubular member from the measured characteristic of the target tubular member.

In some embodiments, the method further includes applying minor and major loads to the target tubular member with the testing apparatus, and in some embodiments the measured characteristic of the target tubular member is a variance between depths of permanent indentations formed in the target tubular member by the applications of the minor and major loads. In some embodiments, the major load is in the range of about 500 $kg_f$ to about 3000 $kg_f$. The major and minor loads may be sequentially applied to the target tubular member in a generally perpendicular direction at the same location on the target tubular member. In some embodiments, determining the hardness value includes determining a Rockwell hardness value in accordance with ASTM E-18.

According to another aspect, the disclosure is directed to a down-hole testing apparatus for determining a hardness of tubular members deployed in a wellbore. The down-hole test apparatus includes a probe deployable on a conveyance into the wellbore. An indenting member of the testing apparatus is operable to selectively extend from the probe and to form permanent indentations a target tubular member. A controller including instructions for obtaining measurements of a minor indentation and a major indentation formed in the target tubular member by the respective application of a minor load and a major load with the indenting member to the target tubular member is provided, a communication unit of the down-hole testing apparatus is operable to transmit a signal indicative of the measurements from the probe.

In some embodiments, the controller includes a processor operable to determine a hardness value from the measurements of the minor indentation and the major indentation. In some embodiments, the down-hole testing apparatus further includes an inclination sensor operably coupled to the controller, and the controller may be operable to verify a perpendicular inclination of the indenting member with respect to the target tubular member. In some embodiments, the indenting member includes at least one of a ball indenter tip and a conical indenter tip. The down-hole testing apparatus may further include a hydraulic actuator operably coupled to the indenting member and selectively operable to impart the minor load and the major load to the target tubular member through the indenting member. In one or more exemplary embodiments, the down-hole testing apparatus further includes a conveyance coupled to the probe, wherein the conveyance comprises at least one of a drill string, coiled tubing and wireline.

Moreover, any of the method steps described herein may be embodied within a system including electronic processing circuitry to implement any of the methods, or a in a computer-program product including instructions which, when executed by at least one processor, causes the processor to perform any of the methods described herein.

The Abstract of the disclosure is solely for providing the United States Patent and Trademark Office and the public at large with a way by which to determine quickly from a cursory reading the nature and gist of technical disclosure, and it represents solely one or more embodiments.

While various embodiments have been illustrated in detail, the disclosure is not limited to the embodiments shown. Modifications and adaptations of the above embodiments may occur to those skilled in the art. Such modifications and adaptations are in the spirit and scope of the disclosure.

What is claimed is:

1. A method of evaluating down-hole structures, the method comprising:
   conveying a testing apparatus having an indenting member into a wellbore to position the testing apparatus adjacent a target down-hole structure;
   applying a major load to the down-hole structure with an indenting member of the testing apparatus to permanently form a major indentation in the target down-hole structure;
   maintaining the major load for a predetermined dwell time, wherein the dwell time is predetermined to permit elastic recovery of the target down-hole test structure;
   measuring a characteristic of the major indentation, wherein the characteristic of the major indentation is a depth of the major indentation; and
   determining a hardness value for the target down-hole structure from the characteristic the major indentation.

2. The method of claim 1, wherein characteristic of the major indentation is a depth of the major indentation.

3. The method of claim 2, further comprising:
   applying, prior to applying the major load, a minor load to the indenting member to urge the indenting member to engage the target down-hole structure and to permanently form a minor indentation in the target down-hole structure; and
   measuring a depth of the minor indentation; and
   determining a variance between the depth of the major indentation and the depth of the minor indentation to thereby determine the hardness values for the target down-hole structure.

4. The method of claim 3, further comprising communicating at least one of the depth of the major indentation, the depth of the minor indentation, the variance between the depths of the major and minor indentations and the hardness value to a surface location from the testing apparatus in the wellbore.

5. The method of claim 3, further comprising pre-determining the minor load such that the minor load is sufficient to break through a surface finish on the target down-hole structure such that the indenting member engages a core material of the target down-hole structure upon application of the minor load.

6. The method of claim 1, further comprising orienting the testing apparatus in the wellbore such that the indenting member engages the target down-hole structure in a generally perpendicular manner.

7. The method of claim 6, wherein the testing apparatus is oriented to engage the target down-hole structure within 2 degrees of perpendicular.

8. A method of evaluating tubular members disposed in a wellbore, the method comprising:
   conveying a testing apparatus into the wellbore to position the testing apparatus adjacent a concave surface of a target tubular member;
   measuring a characteristic of the target tubular ember with the testing apparatus; and
   determining a hardness value for the target tubular member from the measured characteristic of the target tubular member, wherein determining the hardness value for the target tubular member comprises applying a correction factor to accommodate for the concave surface.

9. The method of claim 8, further comprising applying minor and major loads to the target tubular member with the testing apparatus, and wherein the measured characteristic of the target tubular member is a variance between depths of permanent indentations formed in the target tubular member by the applications of the minor and major loads.

10. The method of claim 9, wherein or load is in the range of about 500 $kg_f$ to about 3000 $kg_f$.

11. The method of claim 9, wherein the major and minor loads are sequentially applied to the target tubular member in a generally perpendicular direction at the same location on the target tubular member.

12. A down-hole testing apparatus for determining a hardness of tubular members deployed in a wellbore, the down-hole test apparatus comprising:
   a probe deployable on a conveyance into the wellbore;
   an indenting member operable to selectively extend from the probe and to form permanent indentations a target tubular member;
   a controller including instructions for obtaining measurements of a minor indentation and a major indentation formed in the target tubular member by the respective application of a minor load and a major load with the indenting member to the target tubular member;
   a communication unit operable to transmit signal indicative of the measurements from the probe; and
   an inclination sensor operably coupled to the controller, and wherein the controller is operable to verify a perpendicular inclination of the indenting member with respect to the target tubular member.

13. The down-hole testing apparatus of claim 12, wherein the controller comprises a processor operable to determine a hardness value from the measurements of the minor indentation and the major indentation.

14. The down-hole testing apparatus of claim 12, wherein the indenting member comprises one of a ball indenter tip and a conical indenter tip.

15. The down-hole testing apparatus of claim 12, further comprising a hydraulic actuator operably coupled to the indenting member and selectively operable to impart the minor load and the major load to the target tubular member through the indenting member.

16. The down-hole testing apparatus of claim 12, further comprising a conveyance coupled to the probe, wherein the conveyance comprises at least one of a drill string, coiled tubing and wireline.

* * * * *

UNITED STATES PATENT AND TRADEMARK OFFICE
CERTIFICATE OF CORRECTION

PATENT NO. : 10,001,433 B2
APPLICATION NO. : 14/930133
DATED : June 19, 2018
INVENTOR(S) : Joe E. Hess and Andy J. Cuthbert Page 1 of 1

It is certified that error appears in the above-identified patent and that said Letters Patent is hereby corrected as shown below:

In the Specification

Column 1, Line 24 change "at d" to -- and --

Column 1, Line 31 change "die" to -- the --

Column 4, Line 64 change "he" to -- be --

Column 9, Line 9 change "tune" to -- time --

In the Claims

Column 10, Line 42 add -- of -- after "characteristic"

Column 10, Line 43 add -- the -- after "wherein"

Signed and Sealed this
Twenty-eighth Day of August, 2018

Andrei Iancu
*Director of the United States Patent and Trademark Office*